United States Patent [19]
Shigetomi

[11] 4,141,954
[45] Feb. 27, 1979

[54] REACTION TUBE ASSEMBLY FOR AUTOMATIC ANALYZER

[75] Inventor: Sadao Shigetomi, Sagamihara, Japan

[73] Assignee: Olympus Optical Company Limited, Tokyo, Japan

[21] Appl. No.: 844,801

[22] Filed: Oct. 25, 1977

[30] Foreign Application Priority Data

Nov. 2, 1976 [JP] Japan .............................. 51-146851

[51] Int. Cl.$^2$ ............................................. G01N 21/24
[52] U.S. Cl. ..................................... 422/64; 356/246
[58] Field of Search ................ 23/253 R, 259, 230 R; 356/246

[56] References Cited

U.S. PATENT DOCUMENTS

| | | | |
|---|---|---|---|
| 3,589,868 | 6/1971 | Hozumi | 23/253 R |
| 3,592,605 | 7/1971 | Noma et al. | 23/253 R |
| 3,811,841 | 5/1974 | Kassel | 23/253 R |
| 4,003,708 | 1/1977 | Taguchi et al. | 23/253 R |

*Primary Examiner*—R. E. Serwin
*Attorney, Agent, or Firm*—Lerner, David, Littenberg & Samuel

[57] ABSTRACT

An assembly comprises a disc having an annular array of a number of reaction tubes formed adjacent to the periphery thereof. Each reaction tube is U-shaped and has its one end formed as an open-ended reaction chamber and its other end functioning as an air supply port. The link portion between the reaction chamber and the port is made transparent, forming a flow cell which permits the transmission of light which is used for the purpose of analytical determination. The assembly permits treatment with a reagent of a sample for reaction as well as a photometry for colorimetric analysis of the sample solution obtained by the reaction treatment of the sample.

5 Claims, 6 Drawing Figures

REACTION TUBE ASSEMBLY FOR AUTOMATIC ANALYZER

BACKGROUND OF THE INVENTION

The invention relates to a reaction tube assembly for automatic analyzers.

Before describing the invention, it will be appropriate to give a brief description of conventional arrangements with reference to FIGS. 1 to 3. Referring to these Figures, there is shown a conventional automatic analyzer 1 which is associated with a control system 2. On its front side, the analyzer 1 has a shelf 1a which centrally carries a sample disc 3 and also carries a pair of conventional reaction tube discs 4, 5 on the opposite sides thereof (see FIG. 2). The analyzer includes a top panel 1b inside which are housed storage and supply devices 19a, 19b for a dilution solution and a sample solution, respectively, as well as a colorimeter 21 (see FIG. 3) for examining the results of analysis. The analyzer also includes a bottom cabinet 1c within which are housed a thermostat 20 for heating the reaction tubes and drives associated with various parts of the analyzer.

The analyzer 1 is electrically connected with the control system 2 and is responsive to instructions from the latter for its operation. Information representing the analytical results in supplied to the control system 2. The control system 2 includes a control mechanism (not shown) which is designed to perform a programmed operation. On its front side, the system 2 includes a panel 2a on which various meters and dials are mounted, and also includes a recording device 6 which records the resulting analytical information.

Both the sample disc 3 and the reaction tube discs 4, 5 are adapted to rotate intermittently in the directions of arrows a, b and c, respectively, in a synchronous manner so that a plurality of sample vessels 7 (see FIG. 2) which are disposed along the periphery of the disc 3 can be aligned with a plurality of U-shaped reaction tubes 8, 9 which are also disposed along the periphery of the discs 4, 5. If desired, the discs 4, 5 may be driven so that a plurality of reaction tubes 8, 9 rather than a single one of them can be fed in one operation. A sample such as the one used in the clinical examination, chemical specimen, and specimen of animals, plants or minerals is contained in small quantities in the vessels 7, and can be transferred and distributed to the individual reaction tubes 8, 9 by means of two pairs of sample transfer arms 10, 11. It is to be noted that each pair of arms can transfer the sample to up to four reaction tubes in one operation.

The samples transferred and distributed among the reaction tubes 8, 9 move together with the discs 4, 5 while being subjected to an analytical treatment as shown in FIG. 3 so as to be converted into a solution to be examined, until it reaches the position of a pair of suction pipe support arms 12, 13 (see FIG. 2), respectively. At this position, the solution to be examined which is contained in the individual reaction tube 8 or 9 is drawn into the colorimeter 21 (see FIG. 3), which yields analytical information. The control system 2 is designed to control such operation of the analyzer 1 and to record the derived analytical information in a sequential manner.

Considering the operation of the arrangement somewhat more closely, the transfer of the sample from the vessels 7 to corresponding reaction tubes 8, 9 takes place through the movement of the distal end of sample suction and displacement pipes 10a, 10b, 11a, 11b of the arm pairs 10, 11 and through the operation of a pump unit $P_1$ (see FIG. 3). As the pump unit $P_1$ operates, a diluting solution is supplied to the sample from a diluting solution storage and supply device 19a, diluting the sample by a given factor. Referring to FIG. 3, it will be noted that one end of the reaction tubes 8, 9 has an opening of an increased size, thus forming reaction chambers 8a, 9a. The sample is introduced into these reaction chambers and is agitated by the supply of air delivered through the air supply port 8b, 9b which are formed at the other end of the reaction tubes. All of the reaction tubes 8, 9 are immersed in respective thermostat vessels 20 associated with the discs 4, 5, and are suitably heated or maintained at a desired temperature by the temperature control of the thermostat. It will be noted that when the air is supplied, the sample is driven upward into the reaction chambers 8a, 9a and is agitated by the air bubbles, but that when the supply of the air is interrupted, the sample moves down into the bottom of the U-shaped tube, permitting a satisfactory heating by the thermostat vessels. The air supply and its interruption are achieved by providing a pair of cover plates 14, 15 (see FIG. 2) which are located above the discs 4, 5 so as to be movable in the vertical direction or in a direction perpendicular to the plane of the drawing. The cover plates 14, 15 move down to close the ports 8b, 9b only permitting insertion of their individual pipes, and move upward to open the ports. A pair of retaining member 16a, 16b (see FIG. 2) are detachably mounted on the cover plates 14, 15 for positioning the air supply pipe or a reagent supply pipe with respect to the reaction tubes 8, 9.

A suitable quantity of reagent is supplied, at a suitable timing, from the reagent storage and supply device 19b to a reaction tube or tubes by using a pump unit $P_2$ and a pipe (not shown) which is carried by the retaining member 16b. When the sample is supplied with a reagent, it is again subjected to agitation by the air supply and is further heated. The sample treated in this manner provides a solution to be examined, and when it reaches the position of the arm 12 or 13, a suction pump (not shown) draws the solution into a flow cell (see FIG. 3) of the colorimeter 21 for its analytical determination. The latter comprises a lamp 21a, an interference filter 21b, a prism 21c and a detector 21d. The results of analysis are recorded by the recorder 6, and the used solution which has been examined is taken out of the apparatus in a suitable manner. The emptied reaction tubes 8, 9 are cleaned with rinsing water supplied through rinsing water tubes 17, 18 (see FIG. 2) so as to be prepared for the next analyzing cycle.

It will be noted that in the conventional automatic analyzer, the solution to be examined which is contained in a reaction tube must be conveyed to the colorimeter, requiring a transfer apparatus and a cleaning apparatus for the flow cell. This resulted in the complication and the increased size of the general arrangement, and required a troublesome treatment.

SUMMARY OF THE INVENTION

It is an object of the invention to provide a reaction tube assembly for automatic analyzers comprising a disc which includes a plurality of U-shaped reaction tubes each having their bottom portion, located intermediate their reaction chamber and air supply port, made transparent.

In the reaction tube assembly of the invention, the reaction tubes are made transparent in their connecting portion, and hence such portion can be directly utilized with a photometric analyzer such as colorimeter. This avoids the need to locate the photometric analyzer separately and apart from the disc, since it may be advantageously installed in the region of the reaction tube assembly. As a consequence, a transfer apparatus, which has been a necessary part of the system in order to transfer the solution to be examined which is contained in a reaction tube into the analyzer, can be eliminated as well as an apparatus for cleaning the associated parts, thereby yielding a reduction in the process steps and the time required.

BRIEF DESCRIPTION OF THE DRAWINGS

FIG. 6 is an exploded perspective view, illustrating the detail of one exemplary construction of a reaction tube used in the assembly.

DESCRIPTION OF PREFERRED EMBODIMENT

Figure 1:
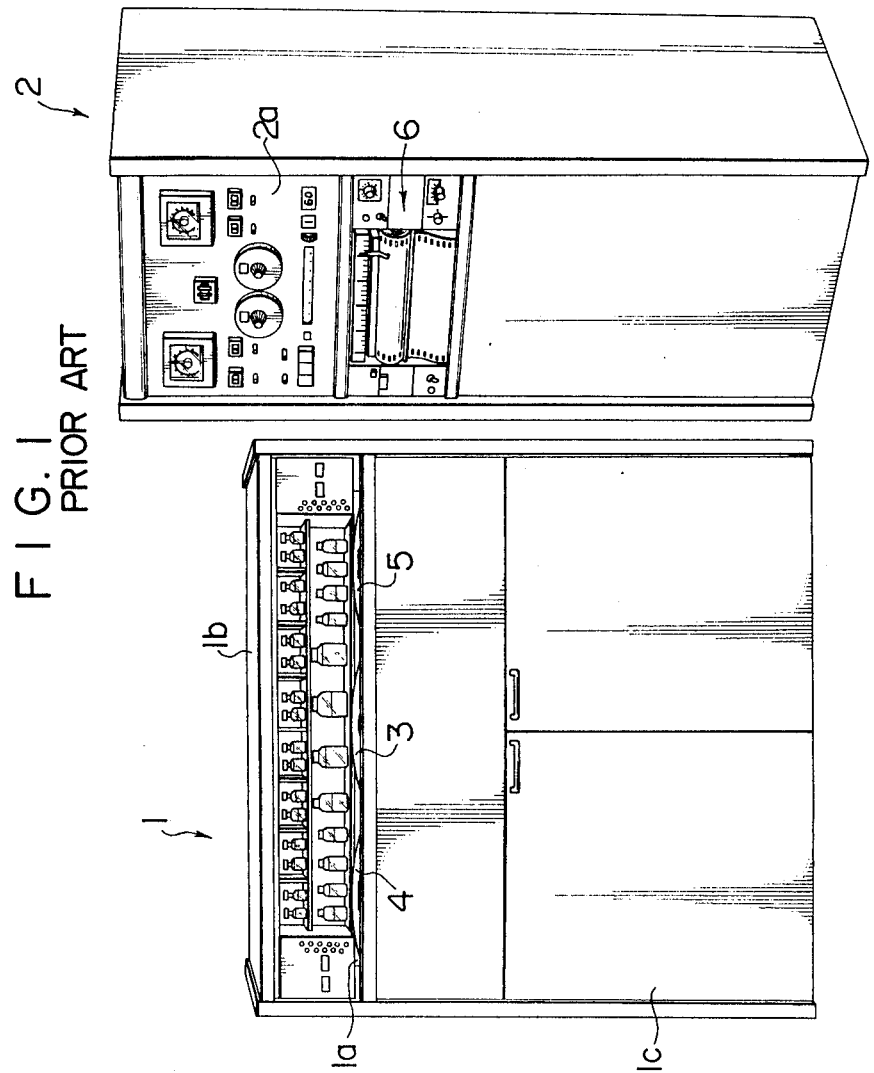
FIGS. 1 and 2 respectively show a perspective view and a plan view of a conventional automatic analyzer.
Figure 2:
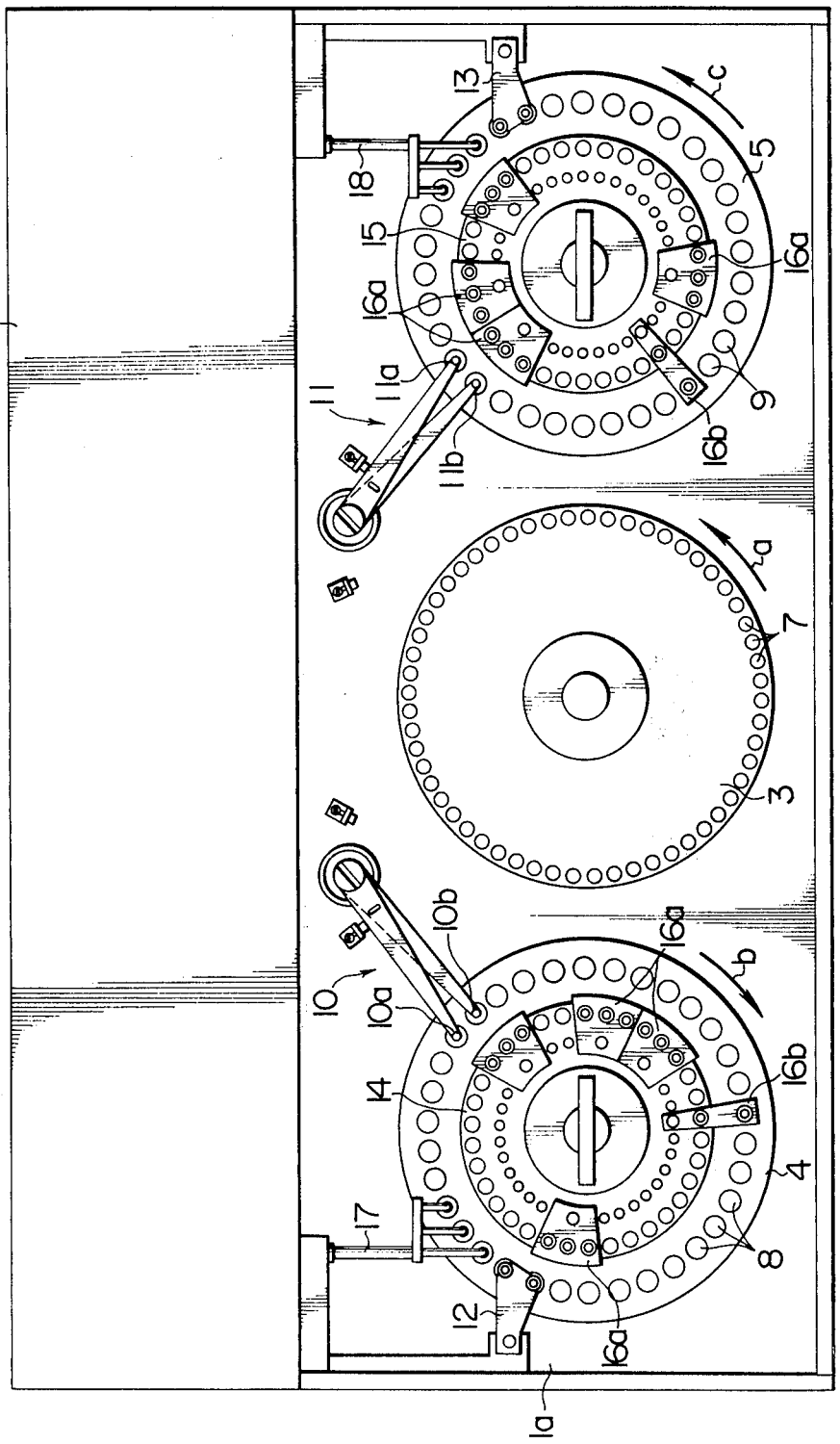
Figure 3:
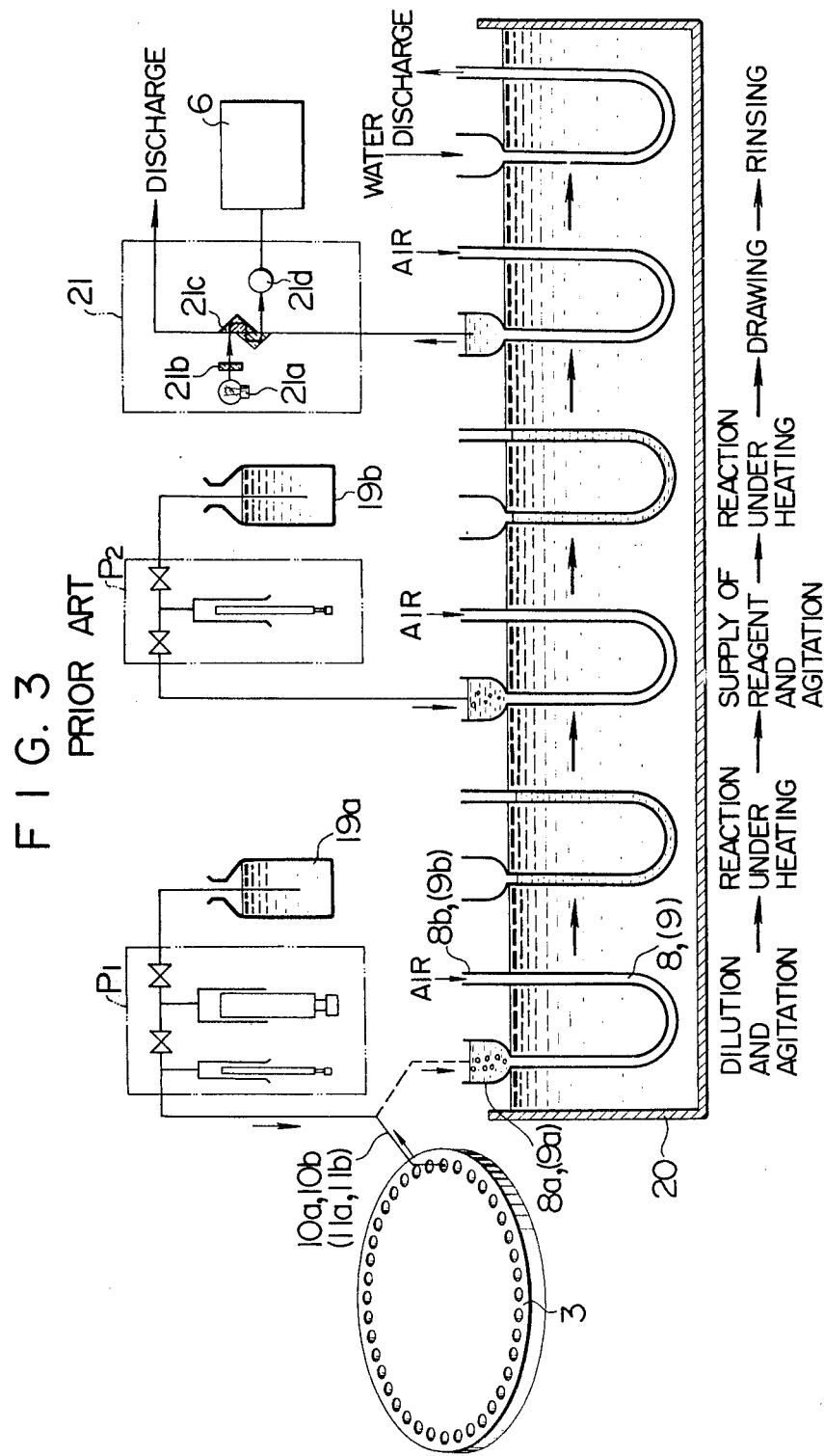
FIG. 3 is an illustration of process steps carried out in the conventional analyzer.
Figure 4:
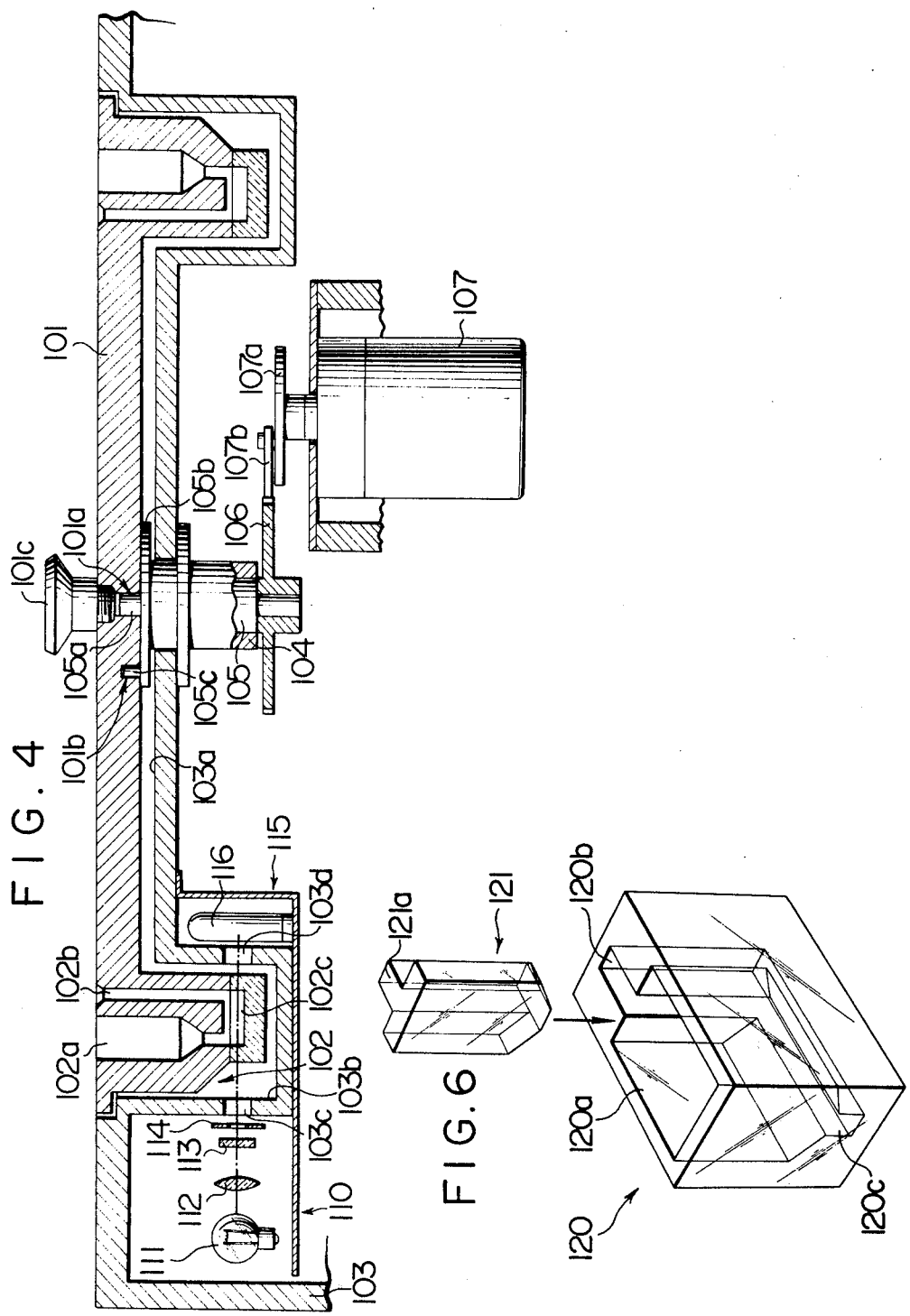
FIG. 4 is a view in cross section showing the reaction tube assembly of the invention combined with its cooperating photometric device.
Figure 5:
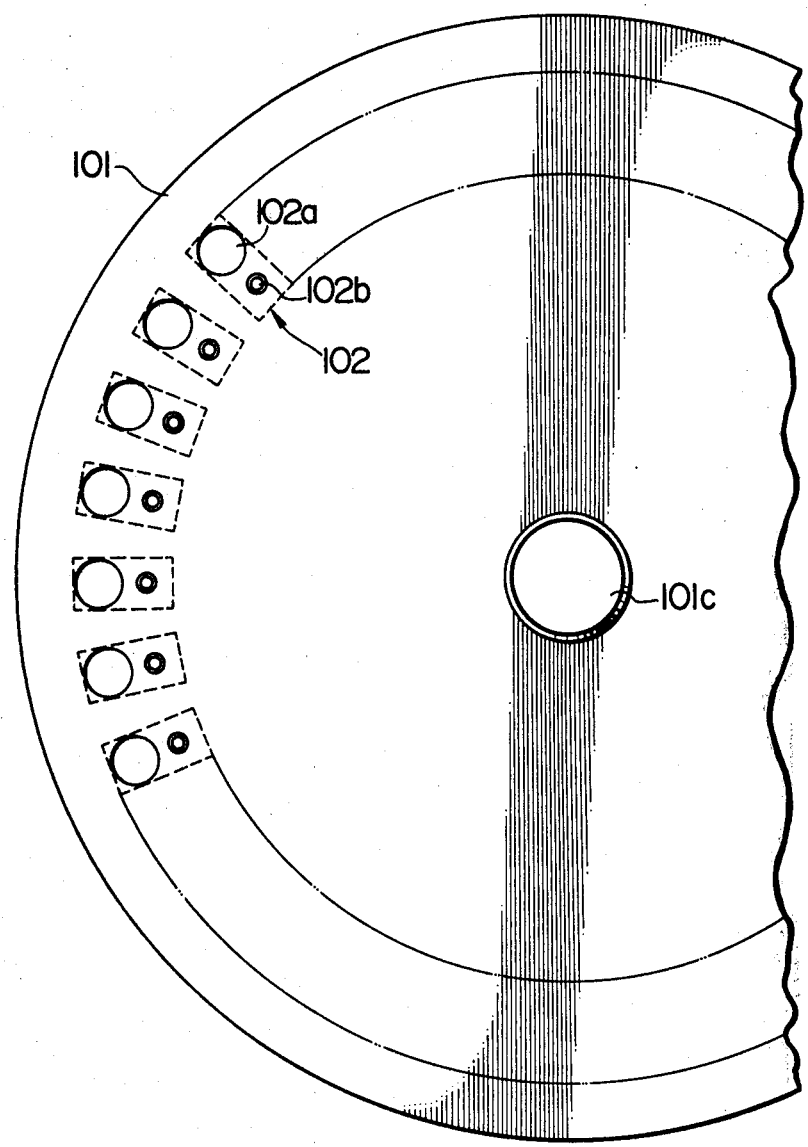
FIG. 5 is a fragmentary plan view of the disc which constitutes the reaction tube assembly.

Referring to FIGS. 4 to 6, there is shown a reaction tube assembly comprising a disc 101 having a plurality of reaction tubes 102 disposed at equal spaced intervals along the periphery thereof. As shown, each reaction tube lies in a radial plane. As shown, the reaction tube 102 is generally U-shaped in configuration, and comprises a reaction chamber 102a, an air supply port 102b, and a link or connecting portion 102c which interconnects the chamber 102a and the port 102b. The link 102c is formed of a transparent material such as glass or plastics, and forms a flow cell.

The automatic analyzer includes a body 103, and the disc 101 is placed on top of the body 103 by engaging an axial bore 101a formed centrally in the lower surface of the disc 101 with the outer end 105a of a drive shaft 105, as shown in FIG. 4. A keyhole 101b is formed in the lower surface of the disc adjacent to the bore 101a, and is engaged by a key 105c formed on the upper surface of a flange 105b which is integral with the drive shaft 105. The disc 101 is centrally formed with a grip 101c on its upper surface, which may be manually gripped and raised to remove the disc from the body 103 for transport in a simple manner.

When placed on the body 103, the disc 101 is rotationally integral with the drive shaft 105 as a result of the interlocking keyhole and key engagement. The drive shaft 105 is rotatably supported in a bearing 104, and fixedly carries a ratchet wheel 106 on its lower end. The ratchet wheel 106 is adapted to be engaged by a feed pawl 107b formed on an output wheel 107a of a motor 107, and thus is intermittently driven as the motor 107 operates. This results in an intermittent rotation of the disc 101 through a given angular increment when the motor 107 is energized.

The body 103 internally houses a light source 110 comprising a lamp 111, lens 112, filter 113 and diaphragm 114, and also internally houses a detector 115 which may be formed by a light receiving element such as phototube 116. The light from the light source 110 passes through an opening 103c formed in a recess 103b of the body 103, then through the solution to be examined which is contained in the cell or the link 102c of the reaction tube 102, and through another opening 103d to be detected by the detector 115.

In operation, a sample to be examined and a reagent or the like are introduced into the individual reaction chambers 102a of the reaction tubes 102. Air is then supplied through the port 102b to agitate the solution, whereby the reaction proceeds. When the solution is ready for photometry, the reaction tube 102 is brought to a position which is indicated by the reaction tube shown on the left-hand side of FIG. 4 so that the light from the source 110 passes through the solution to be examined which is contained in the link 102c, located in the lower portion of the reaction tube, to be detected by the detector 115 for the purpose of photometry. When the photometry of the solution contained in one reaction tube is completed, the motor 107 is operated to rotate the disc 101 through a given angular increment. Thereupon, the reaction tube which has been subjected to the photometry moves out of the photometric position between the source 110 and the detector 115 while another reaction tube containing a reacted solution moves into such position for photometry. In this manner, the solution to be examined which is contained in the individual reaction tubes is sequentially subject to the photometry. It is to be understood that suitable injection nozzles are disposed at given positions to introduce the sample, reagent or the like into the reaction tubes in a sequential manner, and an air cylinder supplies air into them for purpose of agitation to permit the reaction to proceed, thus achieving a continuous photometric operation. After the photometry, the solution is drawn from the individual reaction tubes by a suction nozzle for disposal, and subsequently a rinsing water is supplied into the reaction chamber 102a and then disposed, followed by air drying the tubes. It is to be understood that the body 103 is maintained at a constant temperature so that the reaction proceeds under given conditions.

FIG. 6 shows another construction of the reaction tube which is disposed in an array in the disc. In this Figure, a reaction tube 120 is shaped as an open-top box formed by a transparent material, and includes a reaction chamber 120a with narrow grooves 120b, 120c formed in the right-hand sidewall and the bottom wall thereof. A partition 121 is formed with an elongate rib 121a on its back, which has a thickness substantially equal to the width of the groove 120b but has a length less than the depth of the latter in order to form an air supply port. The partition 121 is tightly fitted into the reaction tube 120 by engaging the rib 121a with the groove 120b so that the rear side of the partition is in close contact with the surface of that sidewall of the tube 120 in which the groove 120b is formed, thus providing a reaction tube which is substantially similar to that shown in FIG. 4. A reaction tube of any special construction can be easily formed in this manner. The partition 121 may or may not be transparent.

What is claimed is:

1. A reaction tube assembly for an automatic analyzer comprising a disc having a plurality of reaction tubes disposed along the periphery thereof, each reaction tube including a reaction chamber which is open at one end of the tube, the other end of the tube being formed as an air supply port with a hollow link providing a communication between the reaction chamber and the air supply port, the link being made transparent to serve as a flow cell.

2. A reaction tube assembly according to claim 1 in which each reaction tube is generally transparent.

3. A reaction tube assembly according to claim 1 in which each reaction tube is formed by a transparent box-shaped body into which a partition is fitted.

4. The assembly of claim 3 wherein the partition is fitted into the body to define a generally U-shaped hollow interior.

5. The assembly of claim 1 further comprising analyzer means including a light source and a sensor means positioned a spaced distance apart; means for stepping said disc in an incremental fashion to position the transparent portion of each tube between said light source and said sensor to permit analysis of the content of each tube.

* * * * *